(12) United States Patent
Ostoich et al.

(10) Patent No.: US 7,765,069 B2
(45) Date of Patent: Jul. 27, 2010

(54) SYSTEMS FOR THE DETECTION OF SHORT AND LONG SAMPLES

(75) Inventors: Vladimir E. Ostoich, Los Altos, CA (US); Kenneth Aron, Burlingame, CA (US); Dennis M. Bleile, San Ramon, CA (US)

(73) Assignee: Abaxis, Inc., Union City, CA (US)

( * ) Notice: Subject to any disclaimer, the term of this patent is extended or adjusted under 35 U.S.C. 154(b) by 1328 days.

(21) Appl. No.: 11/196,941

(22) Filed: Aug. 4, 2005

(65) Prior Publication Data

US 2005/0283318 A1      Dec. 22, 2005

Related U.S. Application Data

(62) Division of application No. 10/273,873, filed on Oct. 18, 2002, now Pat. No. 7,177,767.

(51) Int. Cl.
    G06F 19/00      (2006.01)
    G01N 31/00      (2006.01)
    G01N 33/48      (2006.01)

(52) U.S. Cl. .................... 702/19; 702/127; 356/39

(58) Field of Classification Search .................... None
    See application file for complete search history.

(56) References Cited

U.S. PATENT DOCUMENTS

| | | | |
|---|---|---|---|
| 5,061,381 A | 10/1991 | Burd | |
| 5,122,284 A | 6/1992 | Braynin et al. | |
| 5,186,844 A | 2/1993 | Burd et al. | |
| 5,242,606 A | 9/1993 | Braynin et al. | |
| 5,413,732 A | 5/1995 | Buhl et al. | |
| 5,478,750 A * | 12/1995 | Bernstein et al. | 436/164 |
| 5,590,052 A | 12/1996 | Kopf-Sill et al. | |
| 5,624,597 A | 4/1997 | Buhl et al. | |
| 5,776,563 A | 7/1998 | Buhl et al. | |
| 5,998,031 A | 12/1999 | Buhl et al. | |
| 6,235,531 B1 | 5/2001 | Kopf-Sill et al. | |
| 6,299,839 B1 | 10/2001 | Karunaratne et al. | |
| 6,388,750 B1 * | 5/2002 | Liu et al. | 356/436 |
| 6,628,395 B2 * | 9/2003 | Liu et al. | 356/436 |
| 2005/0196867 A1 * | 9/2005 | Bower et al. | 436/43 |

FOREIGN PATENT DOCUMENTS

| | | | |
|---|---|---|---|
| EP | 1116953 A2 | | 7/2001 |
| JP | 01-129166 | | 5/1989 |
| JP | 10-038898 | | 2/1998 |
| WO | WO 9719340 | * | 5/1997 |
| WO | WO 0036400 | * | 6/2000 |

OTHER PUBLICATIONS

Cembrowski GS., "Thoughts on quality-control systems: a laboratorian's perspective." Clin Chem. May 1997; 43(5):886-92.
Jenny RW, Jackson-Tarentino KY., "Causes of unsatisfactory performance in proficiency testing." Clin Chem. Jan. 2000; 46(1):89-99.
Schembri CT, et al., "Centrifugation and capillarity integrated into a multiple analyte whole blood analyser." J. Autom. Chem. May-Jun. 1995; 17(3):99-104.

* cited by examiner

*Primary Examiner*—Lori A Clow
(74) *Attorney, Agent, or Firm*—Cooley LLP

(57) ABSTRACT

Methods and systems are provided for detecting the accidental use of short and long samples in the clinical analysis of a sample, specimen, or assay. The systems can include a clinical analyzer for determining one or more values for one or more measurable characteristics of a sample. These values are used in combination with reference data stored in a data module to generate a probability that the sample tested is a short sample, a long sample, or an acceptable sample. This probability and/or the status of the sample as a short sample, a long sample, or an acceptable sample are output to a user.

30 Claims, 12 Drawing Sheets

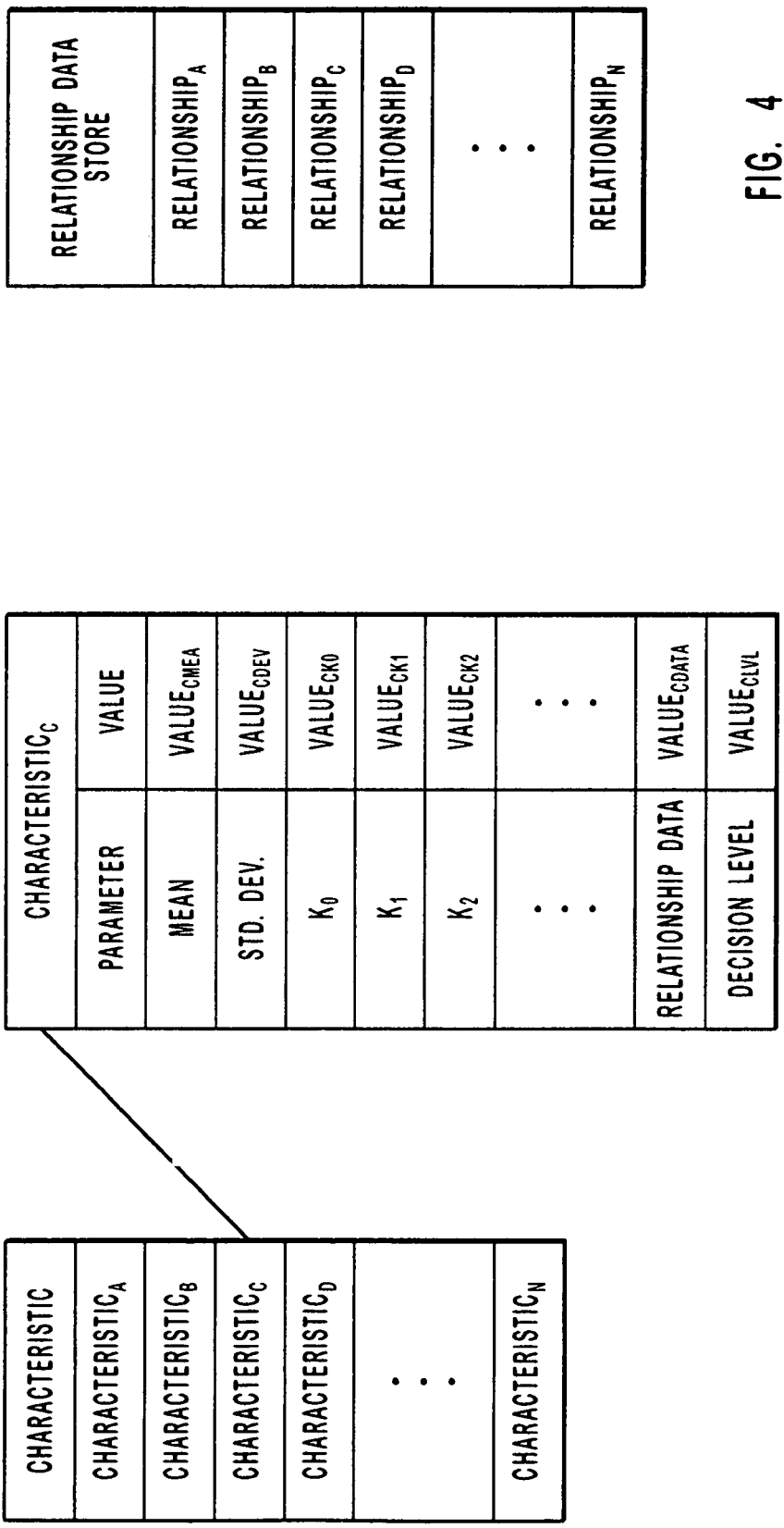

SYSTEMS FOR THE DETECTION OF SHORT AND LONG SAMPLES

This is a divisional of U.S. application Ser. No. 10/273,873, filed 18 Oct. 2002, now U.S. Pat. No. 7,177,767, which is herein incorporated by reference in its entirety.

BACKGROUND OF THE INVENTION

1. The Field of the Invention

The present invention relates generally to systems and methods for analyzing samples or specimens. In particular, the invention relates to systems and methods for detecting the unintentional use of short and long samples in the analyses of sample, specimen, or assay fluids.

2. The Relevant Technology

One important physiological test that is frequently performed by medical and veterinary professionals is the detection and quantification of chemical analytes in biological samples or specimens. Biological samples or specimens that can be tested include a variety of biological fluids, such as blood, plasma, urine, sputum, semen, saliva, ocular lens fluid, cerebral fluid, spinal fluid, and amniotic fluid. Of course, other fluids can be similarly tested for analyte presence and concentration, including tissue culture media, food and industrial chemicals, and environmental samples.

Such biological tests of blood plasma and other biological fluids typically require that a sample or specimen be inserted into a clinical analyzer. The biological samples or specimens are typically processed with various intermediate steps before testing, such as mixing with a diluent. Such clinical analyzers are often capable of quantitatively analyzing a variety of different analytes from a single sample or specimen.

One such clinical analyzer utilizes a rotor, which divides fluids into predetermined volumes for analysis in a variety of optical tests or assays. These analyzers are designed to measure volumes of a biological fluid, such as blood, remove cellular components, and mix the fluid with an appropriate diluent for analysis, for example by spectrophotometric testing. Typically, the rotors provide a plurality of discrete volumes of sample or specimen in separate cuvettes in which the sample or specimen is optically analyzed. One such centrifugal rotor is disclosed in U.S. Pat. No. 6,235,531 to Kopf-Sill et al., incorporated herein by reference.

Although clinical analyzers typically dilute the sample or specimen very precisely, both human and machine error can occur, thus providing false readings. In particular, in the measurement of clinical chemistries a phenomenon called "short sample" is a source of very damaging errors. A "short sample" is very difficult to detect, but can have devastating consequences in the diagnosis of illnesses or monitoring of recovery. For example, under some circumstances the dilution is much larger than a nominal one, resulting in measured values proportionally smaller. This is called a "short sample." The cause of this is usually the failure of the equipment or the operator to provide the precise amount of sample or specimen expected by the instruments performing the measurements. Thus, the analytical data will include inaccurately low numbers. Similarly, a low dilution will result in a high concentration of sample or specimen resulting in a "long sample" that provides inaccurately high numbers.

Currently there are no reliable and simple methods to detect the presence of such short or long samples. The only tools available are based on physiology, because for some analytes the body controls the concentration within a relatively narrow window. Measured values below that physiology window are used as indicators of a possible short sample. One example of such a current method is the subjective opinion of a user analyzing the results, who may recognize that a test value falls below or above the standard range. The user may then order a repeat test. However, it is apparent that this method is very imprecise and extremely subjective. Accordingly, there is a need for improved methods and systems to detect the presence of short and long samples.

SUMMARY OF THE INVENTION

The present invention relates to systems and methods for analyzing samples or specimens. In particular, the invention relates to methods for detecting the accidental use of short and long samples in the analyses of sample, specimen, or assay fluids, such as but not limited to biological fluids.

The terms sample and specimen can be used interchangeably herein. A "short sample" is a sample or diluted sample used in an analyzer that erroneously has too small a sample concentration or volume, while a "long sample" is a sample or diluted sample used in an analyzer that erroneously has too large a sample concentration or volume.

In one embodiment of the present invention, a system is adapted to detect whether a short sample was used in determining sample data for one or more measurable characteristics of the sample. The system includes a data module and an evaluation module. The system also optionally includes an analyzer module and an output module. The analyzer module, such as but not limited to a clinical analyzer with various hardware and/or software components and elements, generates sample data, such as but not limited to values for one or more measurable characteristics of the sample, specimen, or assay. Illustratively, the one or more measurable characteristics include the concentration of one or more analytes of the sample, such as blood, plasma, urine, sputum, semen, saliva, ocular lens fluid, cerebral fluid, spinal fluid, amniotic fluid, immuno assays, genomic assays, or other measurable characteristic. Additionally, the one or more measurable characteristics can be any components of drinking water, wastewater, etc. It is contemplated, however, that the sample data may be received from another source, such as previously generated or recorded data.

The data module stores reference data indicative of one or more distributions of reference sample data, such as data indicative of the value of one or more measurable characteristics of the sample in one or more representative populations. Either the data module or the evaluation module can contain the relationship data, which contains information necessary for the evaluation module to utilize the parameter data and sample data to identify the probability that the sample is a short sample, a long sample, and/or an acceptable sample. This data can be stored in one or more data fields on a computer-readable medium stored at the data module or otherwise accessible to the data module.

The evaluation module is adapted to receive the sample data optionally from the analyzer module. The evaluation module also contains an identification module that identifies the particular measurable characteristics for which values are included in the sample data and obtains the appropriate reference data, including parameter data and relationship data, from the data module. The evaluation module then uses the sample data, the parameter data, and relationship data to determine the probability that the analyzed sample is a short sample, long sample, or an acceptable sample.

An illustrative method according to one aspect of the present invention includes a method for identifying whether a sample, specimen, or assay used in an analyzer module, such as but not limited to a clinical analyzer, to determine one or more measurable characteristics of the sample is a short sample, a long sample, or an acceptable sample. The method includes creating a distribution spread; the distribution spread defining the occurrence frequency for each of one or more measurable characteristics, using a statistically significant measured characteristics data set obtained from a representative population for one or more measurable characteristics.

Using the distribution spread, the method includes selecting a distribution maximum value corresponding to the maximum measured characteristic data occurrence frequency and defining the distribution maximum value to be the point at which the probability that a test sample producing data equal to or greater than the distribution maximum value was a short sample is zero percent.

Using this distribution spread, a distribution minimum value corresponding to a point where the occurrence frequency is close to or equal to zero is selected. The distribution minimum value is then defined to be the point at which the probability that a test sample producing data equal to or less than the distribution minimum value was a short sample is one hundred percent. Once this is achieved, one or more parameters are identified that define the distribution spread bounded by the distribution maximum value and the distribution minimum value. Illustratively, the one or more parameters are associated with a curve fit equation defining a curve that approximates the distribution spread between the distribution minimum value and the distribution maximum value. The one or more parameters and at least one sample data determined by the analyzer module are then used to determine the probability that the sample data generated by the analyzer resulted from a short sample.

A similar method, described in further detail hereinbelow, can be used in identifying that a long sample or an acceptable sample was used in determining one or more measurable characteristics of the sample.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof that are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 3 illustrates an exemplary data structure used in the exemplary system, according to one embodiment of the invention, of FIG. 1;

FIG. 4 illustrates another exemplary data structure used in the exemplary system, according to one embodiment of the invention, of FIG. 1;

DETAILED DESCRIPTION OF THE INVENTION

Figure 1:
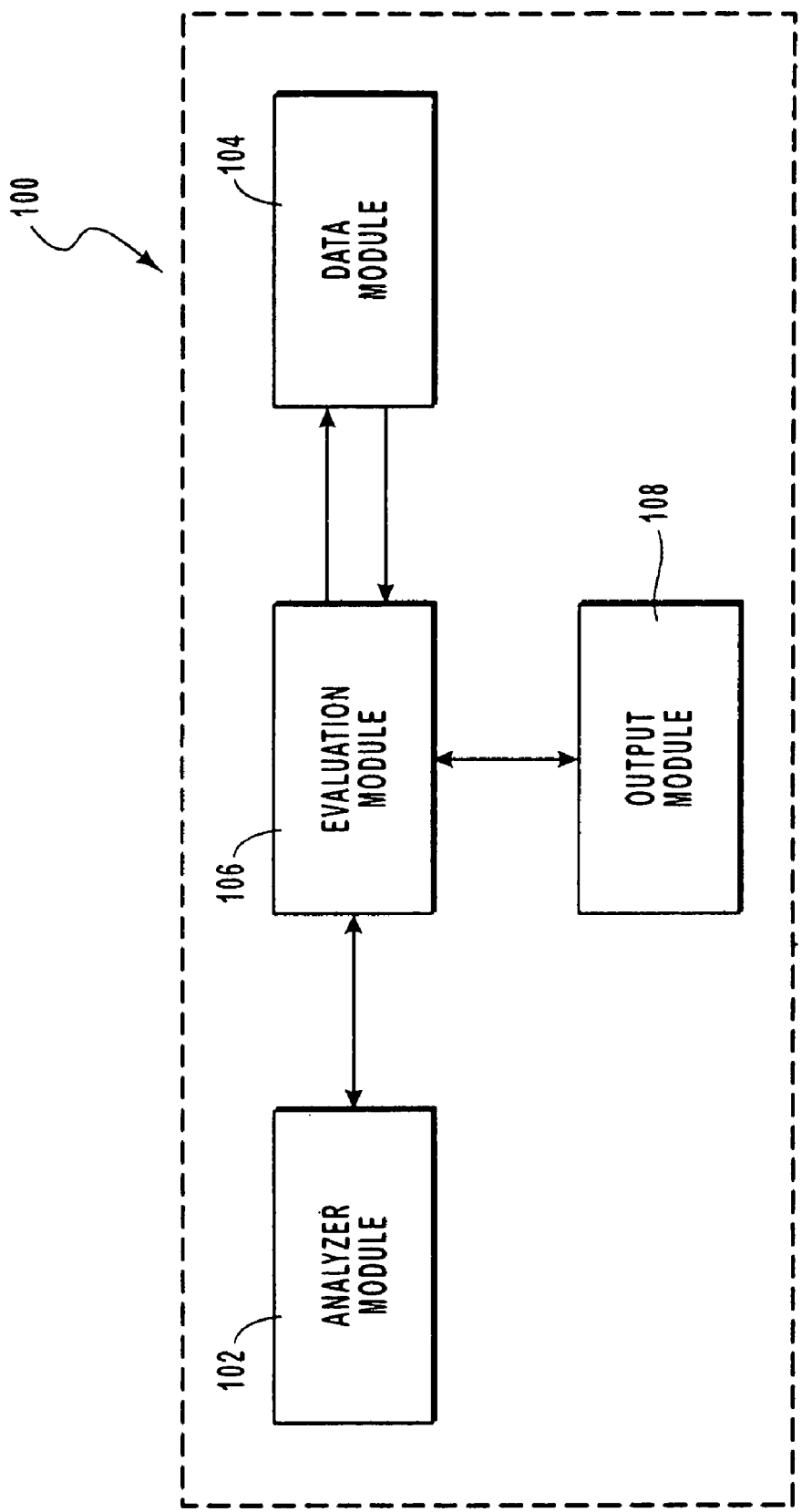
FIG. 1 illustrates an exemplary system according to one embodiment of the invention.

The present invention relates generally to systems and methods for detecting errors in analytical tests of samples or specimens, such as but not limited to blood, plasma, serum, urine, sputum, semen, saliva, ocular lens fluid, cerebral fluid, spinal fluid, amniotic fluid, other biological fluids, or other substances upon which analytical tests are to be performed. In particular, the invention relates to detecting whether a sample, specimen, or assay used in an analytical test is a short sample, a long sample, or an acceptable sample.

As used herein, the term "short sample" denotes a sample that has been diluted to a greater degree than occurs in a standard diluted sample, resulting in the values of measurable characteristics of the sample being proportionally smaller than those for a standard sample. This may result from inadequate volume of sample or from an over-supply of reagents or diluents. Similarly, as used herein, the term "long sample" denotes a sample that has been diluted to a lesser degree than occurs in a standard diluted sample, resulting in the total volume being lesser than the standard volume and the resultant values of measurable characteristics of the sample being proportionally larger than those for a standard sample. This may result from an over-supply of sample or from an inadequate volume of reagents or diluents. The term "acceptable sample" is used herein to denote a sample that is neither a short sample nor a long sample, i.e., substantially similar to a nominal sample with nominal volume.

Analytes are substances that are the subject of analysis, such as glucose, sodium, antigens, antibodies, or any other substance to be analyzed within a sample, specimen, or assay. The analytical tests compatible with the invention can determine information about the various analytes in the sample, such as glucose concentration, sodium concentration, antigen concentration, antibody concentration, or the concentration of any other substance to be analyzed with a sample, specimen, or assay. The analytical tests can also determine a variety of other information about a sample, such as values for properties of the sample itself, for example osmolarity, alkalinity, acidity, and the like. Collectively, the analyte and properties of the analyte and/or sample are referred to as "measurable characteristics."

The term "sample data" refers to data collected from an analytical test of a sample, specimen, or assay, such as any information or values for any of the one or more measurable characteristics of the sample, specimen, or assay. For example, a non-exclusive list of sample data, and hence any measurable characteristic includes: total bilirubin (tbil), direct bilirubin (dbil), aspartate amino transferase (ast), creatine kinase (ck), alanine aminotransferase (alt), gamma glutamyl transferase (ggt), alkaline phosphotase (alp), amylase (amy), carbon dioxide ($CO_2$), sodium (Na), postassium (K), chloride (Cl), osmolarity (osmo), blood urea nitrogen (bun), creatinine (cre), glucose (glu), total protein (tp), albumin (alb), calcium (Ca), phosphatase (phos), triglycerides (trig), cholesterol (chol), uric acid (ua), magnesium (Mg), lactate dehydrogenase, serum glutamic-oxaloacetic transaminase (sgot), serum glutamic-pyruvic transaminase (sgpt), alkalinity, acidity, osmolarity, total protein/albumin (tp/alb), blood urea nitrogen/creatinine (bun/cre), and Tetraiodothyron ($T_4$), HDL, total cholesterol, cytoplasmic markers, such as CK-MB and structural proteins, such as but not limited to, Tropomin-I and -T. Additionally, the "sample data" can include data gleaned through immuno-assay, genomic assay, or fluid treatment assay, such as but not limited to water treatment. This list is not exhaustive and is intended merely as being exemplary of the assays that may be performed using the systems and method of the present invention.

One or more of the above sample data, and hence values for any one of the measurable characteristics of the sample, specimen, or assay, can be collected individually or in groupings to provide a more comprehensive analysis of a sample, specimen, or assay for a particular purpose. Three exemplary groupings can include, but not limited to, a general chemistry, which includes albumin, alkaline phosphotase, alanine aminotransferase, amylase, aspartate amino transferase, total bilirubin, blood urea nitrogen, calcium, cholesterol, creatinine, glucose, total protein, total protein/albumin, and blood urea nitrogen/creatinine; a basic metabolic panel, which includes blood urea nitrogen, creatinine, glucose, calcium, carbon dioxide, sodium, potassium, chlorine, osmolarity, and blood urea nitrogen/creatinine; and a simple electrolytes test, which quantifies carbon dioxide, sodium, potassium, and chlorine.

The term "parameter data" as used herein relates to data indicative of a distribution for at least one measurable characteristic of a sample, specimen, or assay or the values that in part define a curve fit to at least a portion of a distribution for sample data in a representative population tested for the sample, specimen, or assay. For example, parameter data can include values such as mean, standard deviation, and other constants for a particular curve fit for the distribution of the at least one measurable characteristic in a representative population of test samples or specimens.

Similarly, the term "relationship data" as used herein relates to data that defines a relationship between the parameter data and the sample data that assists in identifying the sample as a short sample, a long sample, or an acceptable sample. Illustratively, the relationship data can includes suitable data, such as one or more equations that define the type of curve fit used to approximate all or a portion of the distribution. Collectively, the parameter data and the relationship data are referred to as "reference data."

Embodiments of the present invention provide systems and methods that quickly and reliably provide a probability indicative of whether sample data is incorrect because it was generated from a particular sample that was accidentally a short or long sample.

I. Systems

Referring now to the drawings, wherein like structures are provided with like reference designations, the drawings show illustrative systems, methods, and modules of one embodiment of the present invention. The present invention extends to methods, modules, and systems for identifying whether an analyzed sample, specimen, or assay is a short sample, a long sample, or an acceptable sample. The embodiments of the present invention may comprise a special purpose or general-purpose computer including various computer hardware, as discussed in greater detail below.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can include RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions include, for example, instructions and data which cause a general purpose computer, special purpose computer, or special purpose processing device to perform a certain function or group of functions.

FIG. 1 and the following discussion are intended to provide a brief, general description of a suitable computing environment in which an exemplary embodiment of the invention may be implemented. Although not required, the invention will be described in the general context of computer-executable instructions, such as program modules, being executed by one or more computers, optionally in a network environment. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those skilled in the art will appreciate that the invention may be practiced by a single general purpose or special purpose computer device. Alternatively, the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

FIG. 1 depicts an illustrative system 100 that includes an optional analyzer module 102, a data module 104, an evaluation module 106, and an optional output module 108. The dotted line surrounding system 100 illustrates that system 100 is optionally part of a single unit, although it is also contemplated that system 100 can include disparate units connected by way of one or more networks, as represented by the arrows connecting the modules of system 100. These networks include, but are not limited to, a wide area network, a local area network, the Internet, or other communication link that allows data to be transmitted from one module to another.

The analyzer module 102 is adapted to generate sample data that is used by evaluation module 106, which is in communication with data module 104, to determine whether the sample data of a tested sample, specimen, or assay is the result of a short sample, a long sample, or an acceptable sample. In this manner, system 100 provides a mechanism through which sample data can be identified as being accurate or inaccurate, and thereby reliable or not.

As shown in this illustrative embodiment, system 100 includes analyzer module 102. The analyzer module 102 is adapted to determine or generate sample data of a tested sample, specimen, or assay. Illustratively, analyzer module 102 generates values for one or more measurable characteristic of the tested sample, specimen, or assay. The analyzer module 102 includes various hardware and/or software components and elements that facilitate the performance of the above recited function, such as but not limited to, an electrochemical analyzer. Various types of analyzers are currently available or may be developed in the future to perform the function of analyzer module 102, so long as the selected analyzer is capable of determining the sample data.

Illustratively, analyzer module 102, such as but not limited to an electro-optical analyzer, can utilize a conventional laboratory centrifuge. Under the operation of software and/or hardware modules and components included within the conventional laboratory centrifuge, as represented by analyzer module 102, the centrifuge rotates a centrifugal rotor mounted thereto. This centrifugal rotor includes chambers, passages, and vents in a desired geometric pattern or relationship that facilitate separating cellular components from a test sample, such as a biological sample (e.g. whole blood) as the rotor is rotated under the direction of the software and/or hardware of the centrifuge. Further, the chambers, passages, and vents aid with measuring a precise volume of the test sample (e.g. plasma), mixing the test sample with an appropriate diluent, and delivering the diluted test sample to cuvettes for analysis. Various specialized chambers and channels suitable for use in the rotors of the invention are disclosed in U.S. Pat. No. 5,061,381 to Burd, U.S. Pat. No. 5,122,284 to Braynin, U.S. Pat. No. 5,186,844 to Burd, and U.S. Pat. No. 5,242,606 to Braynin, which are expressly incorporated herein by reference.

In one configuration, the test sample or fluid delivered to the cuvettes reacts with a reagent. The reagents used are well known and amply described in the patent and scientific literature, such as but not limited to those reagents described in U.S. Pat. No. 5,413,732 to Buhl et al., U.S. Pat. No. 5,998,031 to Buhl et al., U.S. Pat. No. 5,776,563 to Buhl et al., and U.S. Pat. No. 5,624,597 to Buhl et al., each of which is expressly incorporated herein by reference.

The reactions between the test sample and the reagents in the test curette result in some detectable or measurable changes that may be related to the presence and/or amount of a particular measurable characteristic of the test sample, specimen, or assay. For instance, the addition of the sample to the test curette may modulate a reaction or other change that results in a change in color, fluorescence, luminescence, or other detectable change in the sample, specimen, or assay.

Over the course of a reaction, or following a reaction, the test curettes are analyzed to detect for one or more of the measurable characteristics, such as one or more analytes within the sample, specimen, or assay or particular properties of the sample, specimen, or assay, such as but not limited to, those described herein and such others known to one skilled in the art in light of the teaching contained herein.

In one configuration, the rotor is transparent so that the presence and distribution of the sample, specimen or assay, cellular components thereof, and/or reagents, may be observed within the various internal chambers, passages, and/or cuvettes. Optionally, when the rotor is opaque or non-transparent, it is desirable to have one or more suitable optical paths formed within the rotor so that the contents of the cuvettes may be observed. In either case, the sample, specimen or assay is analyzed spectrophotometrically, fluorometrically, using chemiluminescence, using light scatter technology, or through use of other measuring instruments and technologies, and appropriate hardware and/or software, as known to those skilled in the art to generate sample data representative of one or more measurable characteristics of a sample, specimen or assay. In some cases, immunoassays and other specific binding assays may be performed within the cell-free fluid collection chamber or within cuvettes that are connected to the collection chamber.

Figure 2:
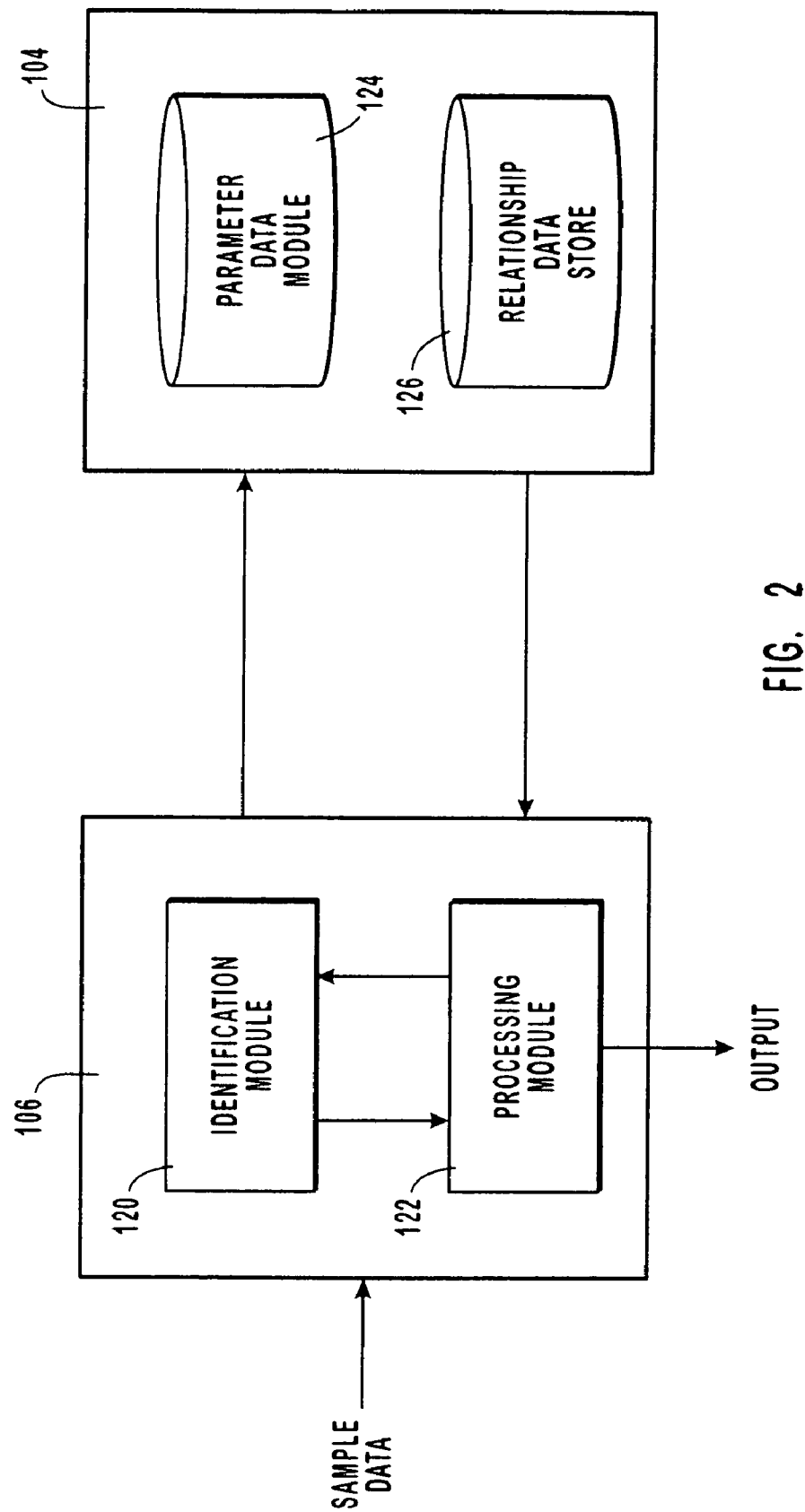
FIG. 2 illustrates a more detailed representation of a portion of the exemplary system, according to one embodiment of the invention, illustrated in FIG. 1.

Referring now to FIG. 2, depicted is a more detailed representation of evaluation module 106 and data module 104. As shown, data module 104 includes parameter data store 124 and relationship data store 126. Although reference is made to data module 104 including parameter data store 124 and relationship data store 126, one skilled in the art can appreciate that data module 104 may access parameter data and relationship data stored in one or more other data stores that are local or remote from system 100 but accessible by data module 104. For example, data module 104, parameter data store 124, relationship data store 126, or another data store can include one or more databases having hierarchal, relational, flat, or other database structures, while including related database management systems (not shown). Further, data module 104, parameter data store 124, relationship data store 126, or another data store can utilize modular or fixed memory, volatile or non-volatile memory, magnetic storage media, CDRW, optical storage media, or other mass storage for storing the information and data described herein.

As shown in FIG. 3, parameter data store 124 can store reference data as a list of the various analytes, properties, or characteristics that can be identified in a test sample, specimen or assay, i.e., $Characteristic_A$-$Characteristic_N$. Each $Characteristic_A$-$Characteristic_N$ includes one or more parameters defining all or a portion of a distribution, such as a distribution curve fit, for that specific measurable characteristic. As shown, such parameters of the reference data can include, but are not limited to, mean, standard deviation, constants $K_0$, $K_1$, $K_2$, or other mathematical equations relating to characteristics or properties of the sample, specimen or assay. Each parameter includes a related value, $Value_{CMean}$, $Value_{CSTD}$, $Value_{CK0}$, $Value_{CK1}$, $Value_{CK2}$, etc., or other values known to those skilled in the art in light of the teaching contained herein. These parameters and values can be stored in one of more fields, with the particular organization of the fields, the parameters, and values, being a data structure. Additionally, parameter data store 124 includes one or more relationship data parameters that define the particular relationship data stored in relationship data store 126 to be used to generate a probability of the sample being a short sample, a long sample, and/or an acceptable sample based upon the measurable characteristics to be tested. For instance, the relationship data parameter includes a Value$_{CData}$ value. Alternatively, the relationship data parameter can be one or more equations that return a probability given a value or values for a particular characteristics or properties of the test sample, specimen, or assay.

Additionally, parameter data store 124 further includes a decision level parameter that defines a threshold value that limits whether the tested sample, specimen or assay is a short sample, a long sample, and/or an acceptable sample. For instance, the value of the decision level parameter, Value$_{CLVL}$, can be a threshold percentage below which the sample is considered a short sample or a long sample. This value can be variably defined by an operator or user of system 100 or hardcoded into system 100. For instance, the threshold value can be obtained from short sample or long sample cumulative distributions indicating the population of values of the probability that a sample is a short sample or a long sample. For instance, an exemplary cumulative short sample distribution for a general panel of 12 chemistries sample is indicated in Table 1.

TABLE 1

| P(Short Sample) | Frequency | Cumulative % |
|---|---|---|
| 0.0% | 0 | .00% |
| 2.5% | 26 | 6.52% |
| 5.0% | 35 | 15.29% |
| 7.5% | 48 | 27.32% |
| 10.0% | 54 | 40.85% |
| 12.5% | 72 | 58.90% |
| 15.0% | 47 | 70.68% |
| 17.5% | 41 | 80.95% |
| 20.0% | 28 | 87.97% |
| 22.5% | 17 | 92.23% |
| 25.0% | 6 | 93.73% |
| 27.5% | 10 | 96.24% |
| 30.0% | 7 | 97.99% |
| 32.5% | 4 | 99.00% |
| 35.0% | 1 | 99.25% |
| 37.5% | 0 | 99.25% |
| 40.0% | 2 | 99.75% |
| 42.5% | 1 | 100.00% |
| 45.0% | 0 | 100.00% |
| More | 0 | 100.00% |

As can be seen from Table 1, provability values larger than 42.5% were not observed in this exemplary sample; however, provability values larger or lesser than 42.5% may be observed for other samples. In the event that a threshold level of 27.5% were selected, then approximately 3.76% of the samples, i.e., 100%–96.24%=3.76% of the samples, will be detected as short samples, even if they are normal or acceptable samples. In contrast, if a threshold level of 42.5% was selected, no false short samples would by detected; however, there is a potential for some real short samples not being detected.

Although reference is made to one specific cumulative distribution associated with one set of short sample probabilities associated with one particular sample, it can be appreciated by one skilled in the art that cumulative distributions can be calculated for long or short samples for a variety of different samples. Further, each cumulative distribution can provide one or more threshold levels that can be selected by a user or hard coded into the system.

As mentioned above, data module 104 includes relationship data store 126. This relationship data store 126, as shown in FIG. 4, includes relationship data, Relationship$_A$-Relationship$_N$, indicative of one or more equations that can be used to generate a probability of the particular characteristic, Characteristic$_A$-Characteristic$_N$, being measured in a sample, specimen, or assay. It can be appreciated that one or more of Characteristic$_A$-Characteristic$_N$ can use the same relationship data, Relationship$_A$-Relationship$_N$, while it is understood that alternatively each characteristic, Characteristic$_A$-Characteristic$_N$ can use different relationship data, Relationship$_A$-Relationship$_N$. Although reference is made to end relationship data, Relationship$_A$-Relationship$_N$ being one or more equations, more generally, the relationship data, Relationship$_A$-Relationship$_N$ can be any one or more parameters that define a relationship between the parameter data and the sample data that assists in identifying the sample, specimen, or assay as at least one of a short sample, a long sample, or an acceptable sample.

Returning to FIG. 2, communicating with data module 104 is evaluation module 106. Evaluation module 106 contains an identification module 120 that is in communication with a processing module 122. Identification module 120 is adapted to receive sample data from analyzer module 102 and determine the specific measurable characteristics identified by the sample data and optionally the values of the same. For example, with reference to FIG. 5, identification module 120 can receive sample data 128 that includes a listing of particular measurable characteristics and associated values, Characteristic$_{ASample}$-Characteristic$_{ASample}$ and Value$_{ASample}$-Value$_{NSample}$ respectively. Although reference is made to a listing of Characteristic$_{ASample}$-Characteristic$_{ASample}$ and Value$_{ASample}$-Value$_{NSample}$, one skilled in the art, in light of the teaching contained herein, can appreciate that such data can be delivered to evaluation module 106 in a variety of different formats.

Upon receiving the sample data, identification module 120 can identify each particular Characteristic$_{ASample}$-Characteristic$_{NSample}$ and obtain the relevant parameter data from data module 104. More specifically, identification module 120 can retrieve parameter data 124, i.e., parameter associated with one or more of Characteristic$_A$-Characteristic$_A$ for the specific identified Characteristic$_{ASample}$-Characteristic$_{NSample}$, whether directly from data module 104 or from some other data module communicating with data module 104, included in the sample data. Additionally, identification module 120 can retrieve the relevant relationship data from relationship data store 126 before delivering the sample data, the parameter data, and the relationship data to processing module 122.

The processing module 122, using the sample data, the parameter data, and the relationship data, generates data indicative of the probability that the test sample analyzed with analyzer module 102 is a short sample, a long sample, or an acceptable sample. This can be achieved as processing module 122 combines the relationship data and the parameter data to generate a probability derived from the probability equation that uses the specific one or more of the measurable characteristics included in the sample data for the test sample, specimen, or assay. Processing module 122 can further combine the probabilities associated with one or more measurable characteristics of the test sample, specimen, or assay to determine whether any combination of the one or more measurable characteristics results in the test sample, specimen, or assay being identified as a short sample, long sample, or acceptable sample.

The evaluation module 106 delivers the results of the analysis to output module 108. The output module 108 presents the results to the user of system 100, such as an administrator, and optionally stores the same for subsequent access or delivery. Presentation of the results can be achieved in a variety of manners, such as an audio notification, visual notification, combination thereof, or the like that the sample is short, long, or acceptable. Illustratively, output module 108 can include a "go/no-go" indicator calibrated to display a particular short sample probability. Such an indicator can use color-coding, such as green, yellow, or red; textual messages; or numerical displays, such as "20% probability" to display the requisite information. The go/no-go indicator can thus quickly relay information to an administrator regarding the short or long sample probability based upon data the administrator has previously entered into the system.

In another configuration, output module 108 can present the results using a video display, such as but not limited to, a video monitor, a cathode ray tube device, or a flat screen device. Alternatively, output module 108 can include one or more light emitting diodes (LED) that indicate whether the sample is short, long, or acceptable. For instance, output module 108 can include three differently colored LEDs, with one LED representative of whether a sample is a short sample, a long sample, or an acceptable sample. In another configuration, each LED is the same color. In still another configuration, a series of LEDs are provided, with a sufficient number of the LEDs being illuminated to illustrate the generated probability value of whether the sample is a short, long, or acceptable sample. In still another configuration, output module 108 includes or communicates with one or more liquid crystal displays that display the generated probability value of whether the sample is a short, long, or acceptable sample.

In addition to the above, output module 108 can generate a hardcopy of the results, whether the results merely state whether the sample is short, long, or acceptable, or provides one or more of (i) a graphical representation of the probability, (ii) details of the calculations associated with the probability, (iii) at what level of dilution or concentration of the sample a short or long sample will be flagged, combinations thereof, or other information relevant to the testing and flagging of a sample as short, long, or acceptable.

In general, output module 108 is one structure capable of performing the function of means for displaying the probability results. Each of the above examples is an illustrative structure of such means. Additional, one skilled in the art in light of the teaching contained herein can identify various other configurations.

The above-described system depicts an illustrative embodiment of the invention only, and other embodiments that are consistent with the scope of the present invention will be understood by one skilled in the art as encompassed within this disclosure. For example, the systems of the invention may exclude the analyzer module and receive input sample data from a separate data source, such as a computer readable medium or administrator input data. In this manner, the systems of the invention can be used to detect the presence of a short or long sample for a variety of sample data sets, including data collected at a previous time or by another group.

II. Methods

Illustrative methods according to the invention are depicted in FIGS. 6-9 and involve multiple steps for identifying that a short, long, or acceptable sample was used in determining sample data in an analyzer module, such as but not limited to a clinical analyzer.

Figures 5, 6:
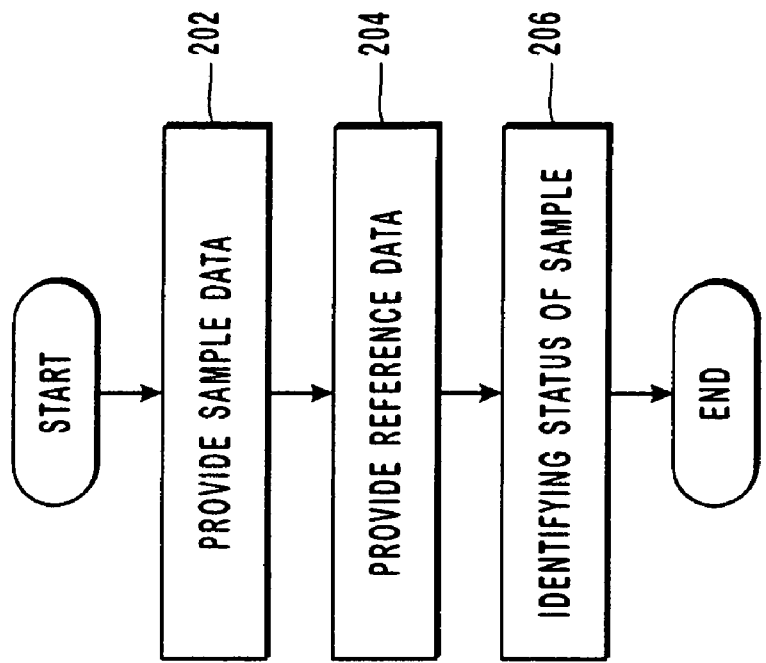
FIG. 5 illustrates still another exemplary data structure used in the exemplary system, according to one embodiment of the invention, of FIG. 1.
FIG. 6 illustrates an exemplary method according to one embodiment of the invention.

Referring to FIG. 6, one exemplary method is therein illustrated. The method includes first providing sample data, as depicted by block 202. Next, parameter data and relationship data related to the sample data are provided, as depicted by block 204. Finally, the status of the sample, i.e., short sample, long sample, and/or acceptable sample, is identified using the sample data and the parameter data, as indicated by block 206. Depending on the particular embodiment of the invention employed, the steps of providing sample data and reference data may be reversed. Each of these steps, as depicted by blocks 202, 204, 206, will be further described hereinbelow with reference to FIGS. 7-9, respectively.

Figure 7:
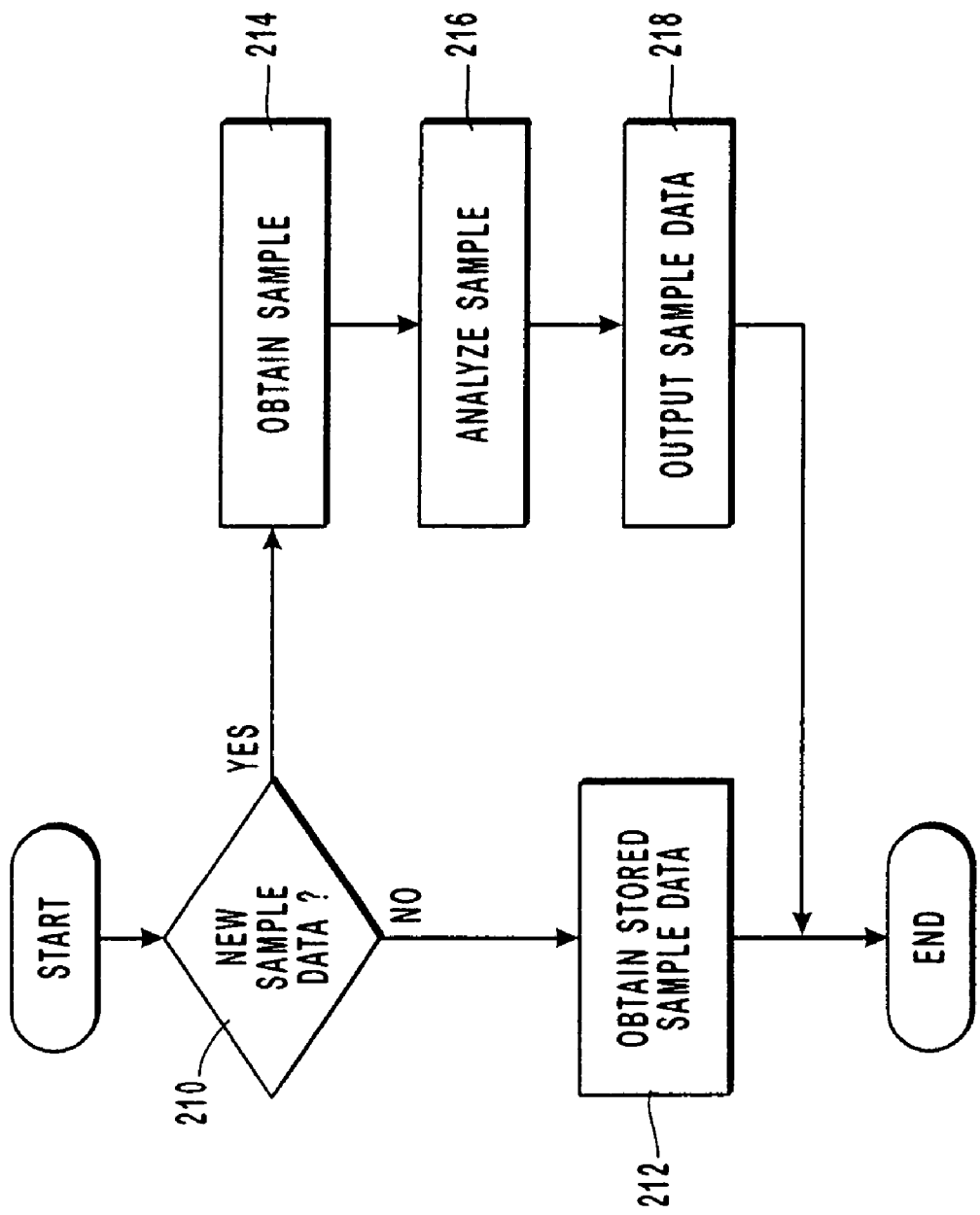
FIG. 7 illustrates yet another aspect of the exemplary method, according to one embodiment of the invention, depicted in FIG. 6.

According to one embodiment of the invention, as represented by decision block 210 in FIG. 7, it is determined whether new or stored sample data is to be obtained. In the event that decision block 210 is in the negative, then stored sample data is obtained, as represented by block 212. The stored sample data can be obtained from a variety of sources, such as but not limited to, from user input, networked sources, or storage media associated with the analyzer module, the evaluation module, and/or the data module. In the event that new sample data is used, which occurs when decision block 210 is in the affirmative, then a sample is first obtained, as represented by block 214. The sample is then analyzed, as represented by block 216, by the analyzer module, and sample data is generated. The sample data is then output from the analyzer module, as represented by block 218. The sample data, whether obtained from a stored source or newly generated is communicated directly to the evaluation module and/or optionally stored for future access and analysis.

Figure 8:
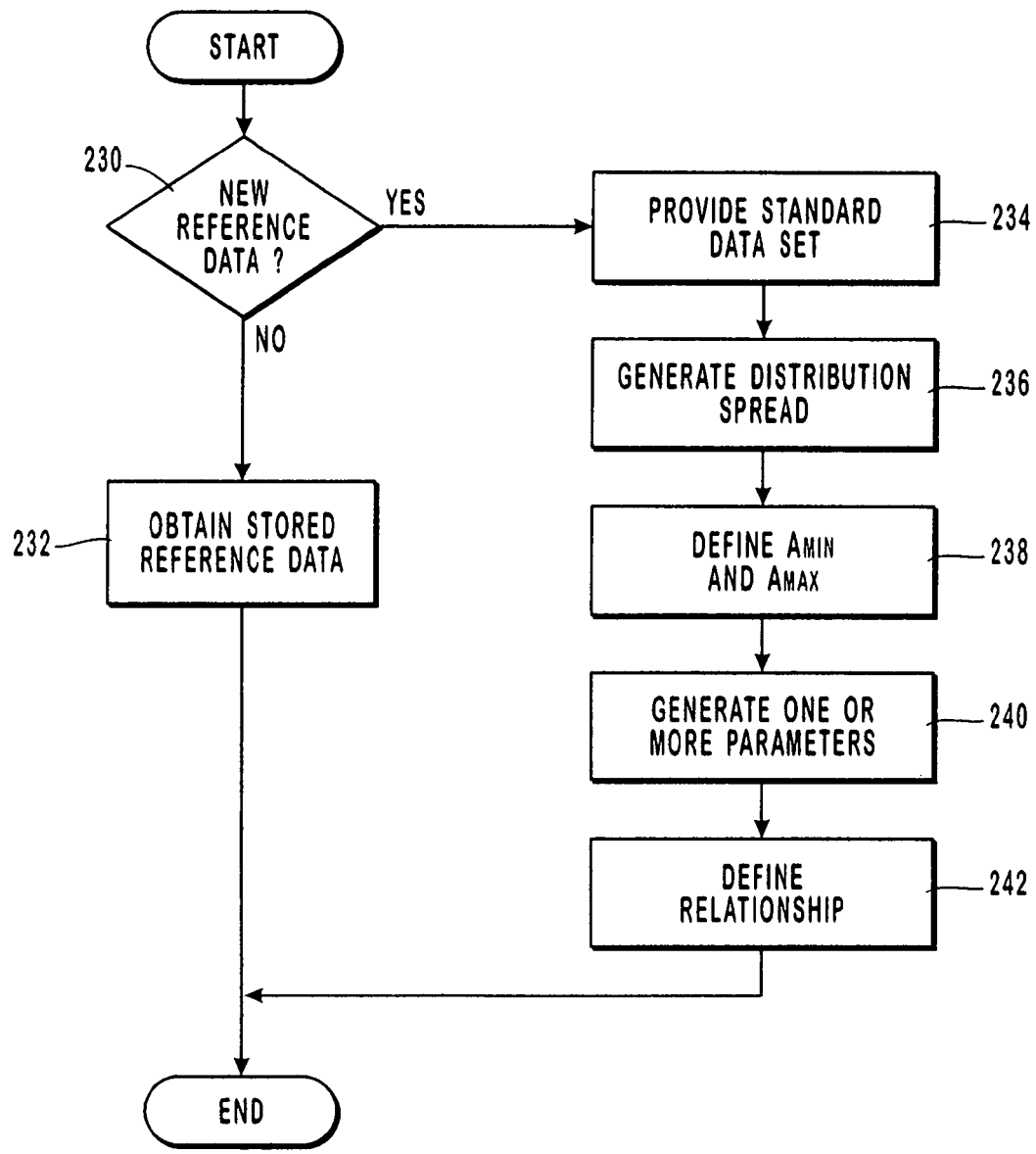
FIG. 8 illustrates yet another aspect of the exemplary method, according to one embodiment of the invention, depicted in FIG. 6.

Referring now to FIG. 8, one method for generating reference data is therein depicted. Initially it is determined whether new reference data or stored reference data is to be used during the analysis and processing, as represented by decision block 230. In the event that decision block 230 is in the negative, then stored reference data is obtained from data module 104, as represented by block 232.

When decision block 230 is in the affirmative, then the method includes providing a statistically significant standard data set from a representative population for one or more of the measurable characteristics included in the sample data, as represented by block 234. This standard data set can be obtained by compiling a statistically significant number of data points to generate a distribution representative of the target population. This standard data set is used to create a distribution spread, as represented by block 236, which is optionally represented as a graphical representation. The distribution spread defines the occurrence frequency for various measured values for each of the one or more measurable characteristics.

Each distribution spread is used to determine a distribution maximum value ("Amax"), as represented by block 238, which corresponds to the maximum occurrence frequency for each specific measurable characteristic included in the sample data, i.e., one Amax value for each specific measurable characteristic. In the case of short sample detection, this Amax is defined to be the point at which the probability that the test sample that produce that specific value for the specific measurable characteristic equal to or greater than this distribution maximum value is a short sample is zero percent (0%). In the case of long sample detection, this Amax is defined to be the point at which the probability that the test sample that produce that specific value for the specific measurable characteristic equal to or less than this distribution maximum value is a long sample is zero percent (0%).

Similarly, a distribution minimum value is selected using the distribution spread to correspond to the point where the occurrence frequency is close to or equal to zero, as also represented by block 238. For short sample detection, the distribution minimum value is then defined to be the point at which the probability that a test sample producing that specific value for the specific measurable characteristic equal to or less than the distribution minimum value is a short sample is one hundred percent (100%). For long sample detection, the distribution minimum value is then defined to be the point at which the probability that a test sample producing that specific value for the specific measurable characteristic equal to or greater than the distribution minimum value is a long sample is one hundred percent (100%). Additionally, for short sample detection the Amin will correspond to a value for the specific measurable characteristic less than Amax whereas in long sample detection the Amin will correspond to a greater value than Amax.

Following identification of Amax and Amin, one or more parameters are defined that identify the portion of the distribution spread bounded by Amax and Amin, as represented by block 240. For example, a curve fit equation, with associated one or more parameters, is generated which fits the distribution spread between the Amax and the Amin. The curve fit equation may take the form of a Gaussian or other distribution equation, and will include at least one or more parameters, such as but not limited to mean, standard deviation, or other constant as required by the curve fit. The parameters that define the path of the curve fit to the distribution spread are the parameter data or reference data stored in parameter data store 124. Although reference is made to Gaussian distribution equation, other forms of curve fit equations can be used and are known to those skilled in the art. For example, and not by way of limitation, other curve fit equations can include exponential equations, logarithmic equations, polynomial equations, Lorentzian equations, Laplacian equations, Poisson equations, or other curve fits equations known to those skilled in the art in light of the teaching contained herein.

The generated curve fit equation between Amax and Amin defines the probability of a sample being a short sample for all values between Amax and Amin. Just as at Amax the probability of a sample being a short sample is 0% and at Amin the probability of a sample being short sample is 100%, the equation for the curve between Amax and Amin is normalized to return a short sample probability between 100% (Amax) and 0% (Amin) for a single characteristic from the distribution curve fit for the single characteristic.

For each set of one or more parameters, relationship data indicative of the relationship between the parameter data and the sample data is defined, as represented by block 242. The relationship data can include one or more probability equations usable to determine, using the parameter data and sample data, the probability that a particular sample datum was determined from a short sample, a long sample, or an acceptable sample. The stored data that defines the probability equation is referred to as relationship data and is stored in the data module or some other data store associated with the system.

Figure 9:
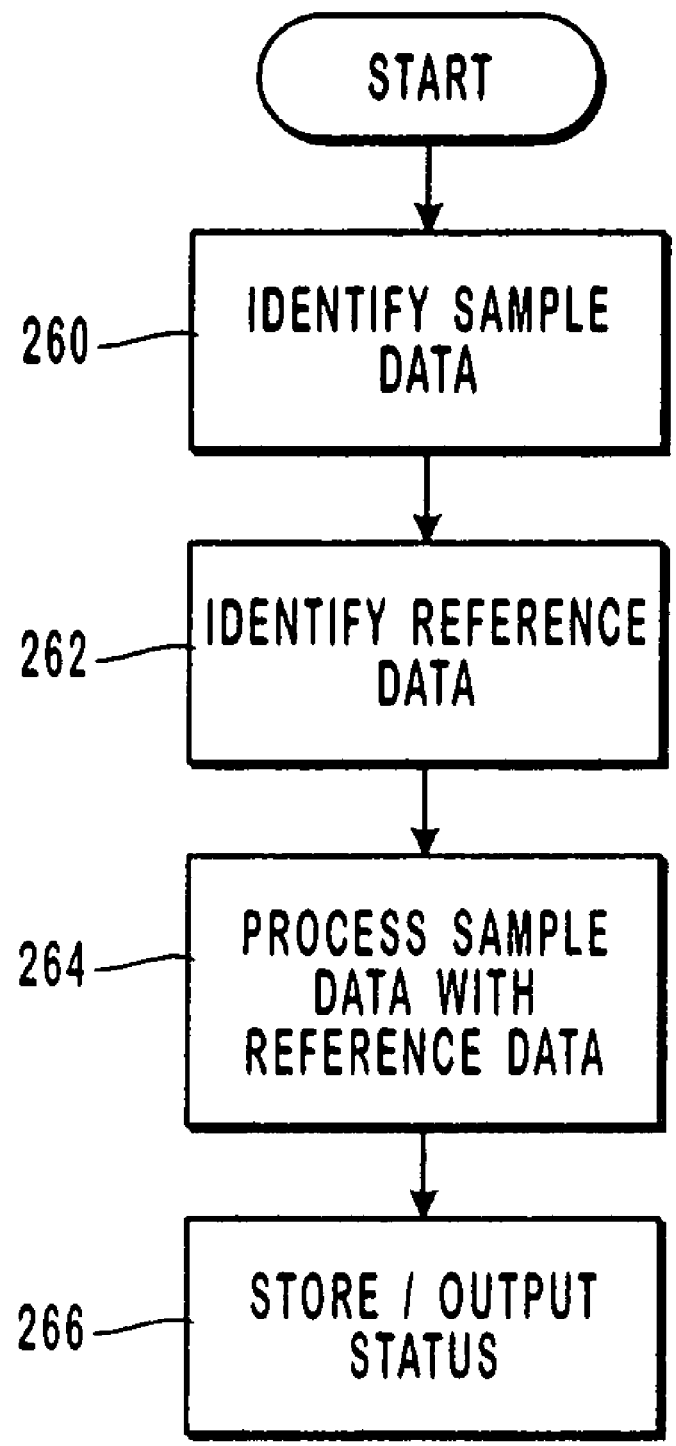
FIG. 9 illustrates yet another aspect of the exemplary method, according to one embodiment of the invention, depicted in FIG. 6.

Referring now to FIG. 9, the method for determining the probability of short, long, or acceptable sample includes using the identification module of the evaluation module to identify the sample data, as represented by block 260, and the reference data, as represented by block 262. The processing module processes the sample data and the reference data and determines the probability of the sample being a short sample, a long sample, or an acceptable sample, as represented by block 264, which is calculated as a numerical value that is converted to a percentage. Finally, the probability is either output or stored, as described hereinabove and represented by block 266.

Additionally, embodiments of the invention also optionally facilitate comparing the calculated probability to a user defined threshold probability value and outputting the result to the user.

Another method according to the invention includes determining the probability of a short, long, or acceptable sample of a sample having any combination of analytes A, B, . . . N using the individual probabilities of short, long, or acceptable sample of the variety of analytes. Thus, where values for more than one measurable characteristic is determined, the short sample probability is preferably defined as the NAND or "not and" of the short sample probabilities of each measurable characteristic normalized by the number of measurable characteristic under consideration, as presented in equation 1.

$$p(\text{Short Sample})=[N-\{p(A)+p(B)+\ldots+p(X)\}]/N \quad \text{(equation 1)}$$

In equation 1, N is the number of measurable characteristics. Of course, other equations can also be used to project the likelihood of a short or long sample based on one or more measured sample, specimen, or assay characteristics.

Similarly, where values for more than one measurable characteristic is determined, the long sample probability is preferably defined as the NAND or "not and" of the long sample probabilities of each measurable characteristic normalized by the number of measurable characteristics under consideration, as presented in equation 2, N is the number of measurable characteristics.

$$p(\text{Long Sample})=[N-\{p(A)+p(B)+\ldots+p(X)\}]/N \quad \text{(equation 2)}$$

Embodiments of the present invention also provide methods for analyzing a statistically significant number of samples for a particular combination of measurable characteristics to calculate the probability distributions for the combination of measurable characteristics for the samples. The distribution of the probabilities can be plotted or tabulated and a threshold limit based on a percentile for flagging the sample can then be established. For example, a test sample having a short sample probability in the 95th percentile or higher can be used to flag that a sample may be a short sample.

Once the model is established for a particular combination of measurable characteristics, the comparison of the calculated probability of short or long sample with the selected threshold can be used as a warning that an insufficient or abnormal amount of sample was used in the analysis. In one embodiment, a threshold level of 20 percent or higher is used. Although this is the case for one embodiment, it can be appreciated that the probability can be identified as between about 18% to about 24%, or from about 30% to about 35%, or from about 48% to about 55%.

Thus, threshold values for flagging a sample can be based both on individual sample data and on other probability functions for a plurality of sample data from different analytes.

Depending on the user preferences and the magnitude of the probabilities, the user will typically repeat the test to confirm that the values measured are real and not the product of a "short sample." Of course, the above methods are not intended to limit the invention as equivalent methods are and steps are contemplated by the invention.

One aspect of the invention includes using the above methods to detect intentional dilutions of biological samples in analytical tests. For example, the above short sample detection methods can be used to identify that a urinalysis, such as is commonly performed as a drug test, and was performed with diluted urine. In this way, the validity of a sensitive analysis can be validated. Therefore, the sample, specimen, or assay can, be treated for one or more antibodies associated with drug abuse with the knowledge that embodiments of the present invention will determine when samples or specimens are valid. Similarly, when embodiments of the present invention are used to test for one or more contaminants in drinking water, wastewater, or other fluid, embodiments of the present invention facilitate the verification process of sample, specimen, or assay authentication.

The following examples are given to illustrate the present invention, and are not intended to limit the scope of the invention. Similarly, the equations provided herein are illustrative and are not intended to limit the possibility of using other equations.

III. Examples

With reference to Table 2, the frequency distribution of various sample fluid data, listed in Examples 1-26, for a human population were obtained and plotted. The point Amax for each distribution was obtained by the method described hereinabove. For each of Examples 1-26, distribution minima and maxima were defined as the minima equals 0 and the maxima equals Amax. A Gaussian curve of the formula presented in equation 3 hereinbelow was found to provide an excellent fit to the data for the defined range. In equation 3, A' is a hypothetical concentration, % is the percent of the population having a U, concentration in that range, as determined by the population histogram used for the determination, and $\sigma A$ is the standard deviation for the Gaussian curve. The mean and constant $k_o$ were also calculated based on the curve.

Thus, when the concentration A is larger than Amax the probability of a short sample is defined as:

$$p(A)=0 \qquad \text{(equation 4)}$$

For a concentration below Amax, the short sample probability was determined according to:

$$p(A) = 1 - \exp\left(.5\left(\frac{A-A\,max}{\sigma A}\right)^2\right) \qquad \text{(equation 5)}$$

Figure 10:
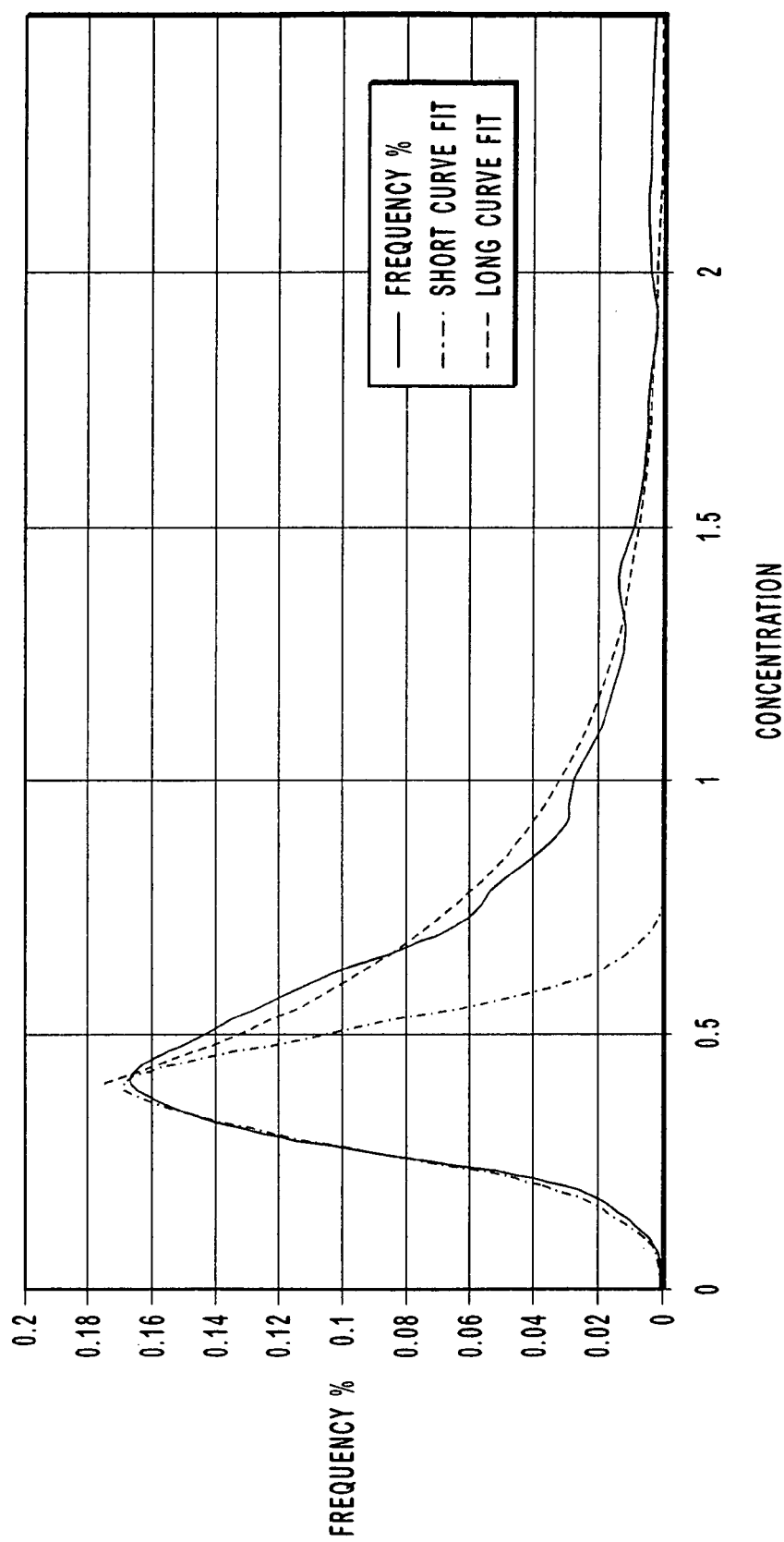
FIG. 10 is a graph depicting an analyte concentration distribution and curves fit to the upper and lower ranges of the analyte concentration distribution.

In order to illustrate the above, FIG. 10 depicts the frequency distribution for total bilirubin concentration (tbil) as used to create the data in Example 1. The line denoted as "Short curve fit" depicts a Gaussian curve fit set to the frequency distribution for A<Amax. As can be clearly seen, the Gaussian curve fits the frequency distribution for A<Amax very well but is a poor fit for A>Amax.

Examples 27-52

In contrast, for the detection of a long sample the portion to the right of Amax is the area of interest, because samples with lower concentrations than Amax will have limited discriminating values in terms of the detection of a long sample. For these concentrations, either a Gaussian distribution as defined above or an exponential distribution as defined by equation 6 below was fitted to the data.

TABLE 2

$$\% = k_0 \cdot \exp\left(-.5\left(\frac{A'-mean}{\sigma A}\right)^2\right) \qquad \text{(equation 3)}$$

| Example | Analyte | Equation for A < Amax | Mean | σA | K₀ |
|---|---|---|---|---|---|
| 1 | total bilirubin (tbil) | Equation 3 | 0.39 | 0.11 | 0.17 |
| 2 | direct bilirubin (dbil) | Equation 3 | 0.1 | 0.07 | 0.51 |
| 3 | aspartate amino transferase (ast) | Equation 3 | 16.5 | 4.0 | 0.165 |
| 4 | creatine kinase (ck) | Equation 3 | 20 | 8 | 0.061 |
| 5 | alanine aminotransferase (alt) | Equation 3 | 12.5 | 4.0 | 0.153 |
| 6 | gamma glutamyl transferase (ggt) | Equation 3 | 75 | 30 | 0.2 |
| 7 | alkaline phosphotase (alp) | Equation 3 | 73 | 17.5 | 0.136 |
| 8 | amylase (amy) | Equation 3 | 36.5 | 11 | 0.185 |
| 9 | carbon dioxide (CO₂) | Equation 3 | 25.5 | 4.5 | 0.1 |
| 10 | sodium (Na) | Equation 3 | 139 | 3.8 | 0.12 |
| 11 | potassium (k) | Equation 3 | 4.15 | 0.49 | 0.155 |
| 12 | chloride (Cl) | Equation 3 | 105 | 5 | 0.275 |
| 13 | osmolarity | Equation 3 | 282 | 10.5 | 0.168 |
| 14 | blood urea nitrogen (bun) | Equation 3 | 13.5 | 5 | 0.164 |
| 15 | creatinine (cr) | Equation 3 | 0.83 | 0.26 | 0.24 |
| 16 | glucose (glu) | Equation 3 | 99 | 17 | 0.225 |
| 17 | total protein (tp) | Equation 3 | 7.6 | 1.15 | 0.225 |
| 18 | albumin (alb) | Equation 3 | 4.5 | 1.1 | 0.275 |
| 19 | calcium (ca) | Equation 3 | 9.3 | 0.86 | 0.175 |
| 20 | phosphatase (phos) | Equation 3 | 3.35 | 0.8 | 0.165 |
| 21 | triglycerides (trig) | Equation 3 | 87 | 23 | 0.078 |
| 22 | cholesterol (chol) | Equation 3 | 178 | 34 | 0.172 |
| 23 | Uric acid (ua) | Equation 3 | 6.0 | 1.5 | 0.19 |
| 24 | magnesium (Mg) | Equation 3 | 1.76 | 0.25 | 0.15 |
| 25 | tp/alb | Equation 3 | 1.77 | 0.14 | 0.195 |
| 26 | bun/cre | Equation 3 | 16.5 | 5.5 | 0.139 |

$$\% = k_0 \cdot \exp^{\left(\frac{-(A'-mean)}{\sigma A}\right)} \quad \text{(equation 6)}$$

The mean, standard deviation, and constant $k_0$ were determined for the curve and are presented in Examples 27-52 below.

TABLE 3

| Example | Analyte | Equation for A > Amax | Mean | σA | $k_0$ |
|---|---|---|---|---|---|
| 27 | total bilirubin (tbil) | equation 5 | 0.41 | 0.35 | 0.17 |
| 28 | direct bilirubin (dbil) | equation 5 | 0.1 | 0.07 | 0.52 |
| 29 | aspartate amino transferase (ast) | equation 5 | 16.5 | 10.0 | 0.18 |
| 30 | creatine kinase (ck) | equation 5 | 60 | 80 | 0.14 |
| 31 | alanine amino-transferase (alt) | equation 5 | 12.5 | 12.0 | 0.153 |
| 32 | gamma glutamyl transferase (ggt) | equation 5 | 75 | 45 | 0.23 |
| 33 | alkaline phosphotase (alp) | equation 5 | 73 | 45 | 0.15 |
| 34 | amylase (amy) | equation 5 | 36.5 | 29 | 0.2 |
| 35 | carbon dioxide ($CO_2$) | equation 2 | 25 | 3.6 | 0.1 |
| 36 | sodium (Na) | equation 5 | 139 | 2.3 | 0.23 |
| 37 | potassium (k) | equation 5 | 4.4 | 0.49 | 0.135 |
| 38 | chloride (Cl) | equation 5 | 105 | 3 | 0.25 |
| 39 | osmolarity (osmo) | equation 5 | 282 | 9.5 | 0.185 |
| 40 | blood urea nitrogen (bun) | equation 5 | 14.5 | 13.5 | 0.15 |
| 41 | creatinine (cr) | equation 5 | 0.83 | 0.28 | 0.28 |
| 42 | glucose (glu) | equation 5 | 99 | 40 | 0.23 |
| 43 | total protein (tp) | equation 2 | 7.7 | 0.65 | 0.23 |
| 44 | albumin (alb) | equation 2 | 4.275 | 0.45 | 0.285 |
| 45 | calcium (ca) | equation 2 | 9.1 | 0.65 | 0.19 |
| 46 | phosphatase (phos) | equation 5 | 3.5 | 1.3 | 0.165 |
| 47 | triglycerides (trig) | equation 5 | 87 | 115 | .075 |
| 48 | cholesterol (chol) | equation 2 | 178 | 60 | 0.17 |
| 49 | uric acid (ua) | equation 5 | 6.0 | 3.5 | 0.19 |
| 50 | magnesium (mg) | equation 2 | 1.74 | 0.32 | 0.15 |
| 51 | tp/alb | equation 5 | 1.5 | 0.3 | 0.55 |
| 52 | bun/cre | equation 5 | 10 | 10 | 0.29 |

In order to determine the probability of a long sample, the probability of a long sample for any given concentration of an analyte A, p(A), is defined as follows:

for A<Amax $$p(A) = 0 \quad \text{(equation 7)}$$

for A>Amax, $$p(A) = 1 - \exp^{\left(\frac{-(A'-mean)}{\sigma A}\right)} \quad \text{(equation 8)}$$

In addition to illustrating the curve fit for the short sample analysis, FIG. 10 depicts the frequency distribution for total bilirubin concentration (tbil) as used to create the data in Examples 1 and 27. The line denoted as "Long curve fit" depicts a Gaussian curve fit set to the frequency distribution for A>Amax. As can be clearly seen, the Gaussian curve fits the frequency distribution for A>Amax very well, whereas it is a poor fit for A<Amax.

Examples 53-54

Figure 11:
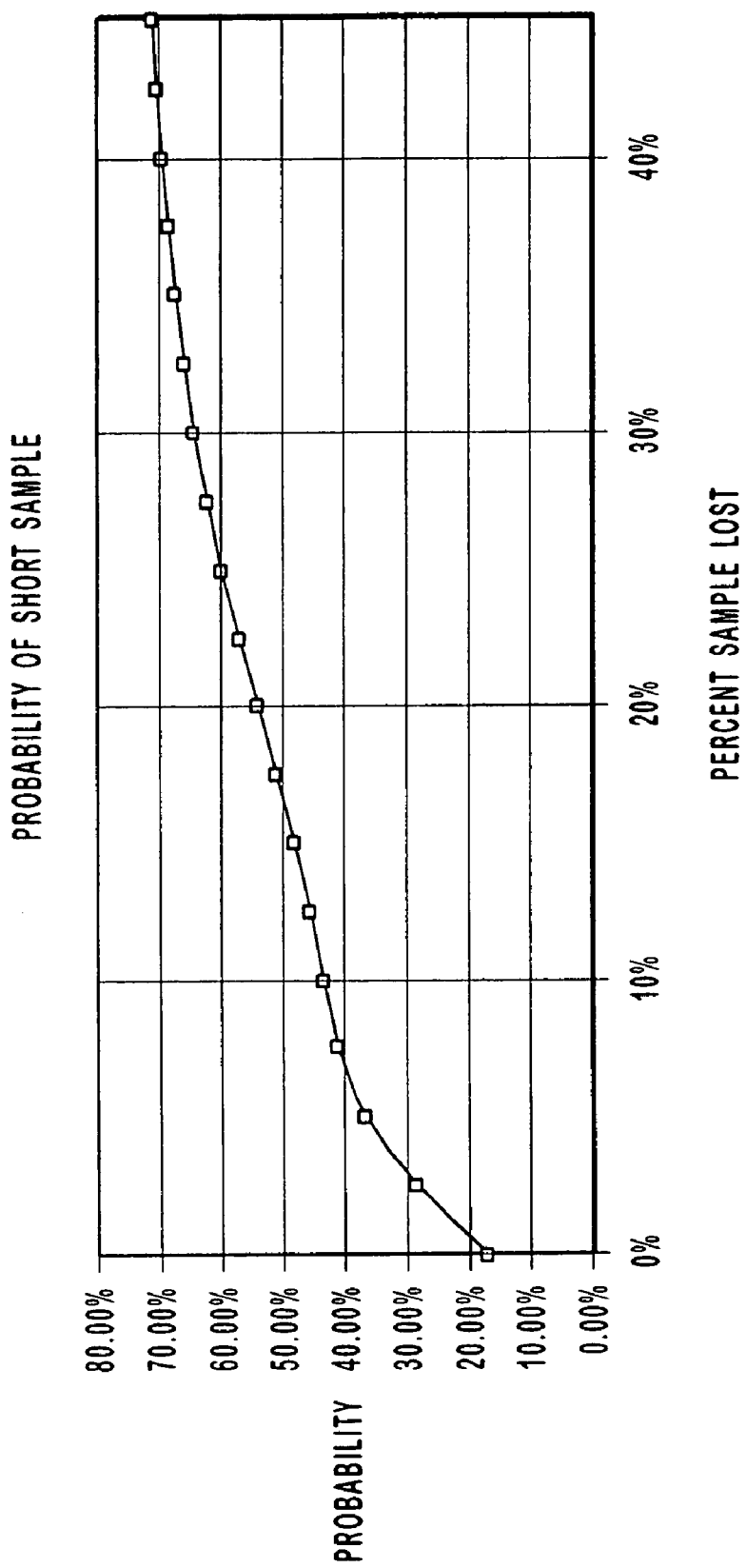
FIG. 11 is a graph depicting the probability of a short sample based on theoretically enlarged sample sizes.

FIG. 11 (Example 53) illustrates the theoretical short sample probability for a sample data set collect for the MetLyte8 collection of analytes and fluid data, including blood urea nitrogen, creatinine, glucose, creatine kinase, carbon dioxide, sodium, potassium, chlorine, osmolarity, and blood urea nitrogen/creatinine. A sample analyte or sample fluid characteristic value data set is obtained for an accurately sized and diluted sample. The sample data set is then hypothetically multiplied times a sequentially increasing percent sample lost, i.e. 10%, 20%, etc., to obtain lower data results. The probability of short sample at percent sample lost is calculated for each datum and they are all then combined through Equation 5 that calculates the probability that a short sample would occur for percent samples lost up to 45 percent.

Figure 12:
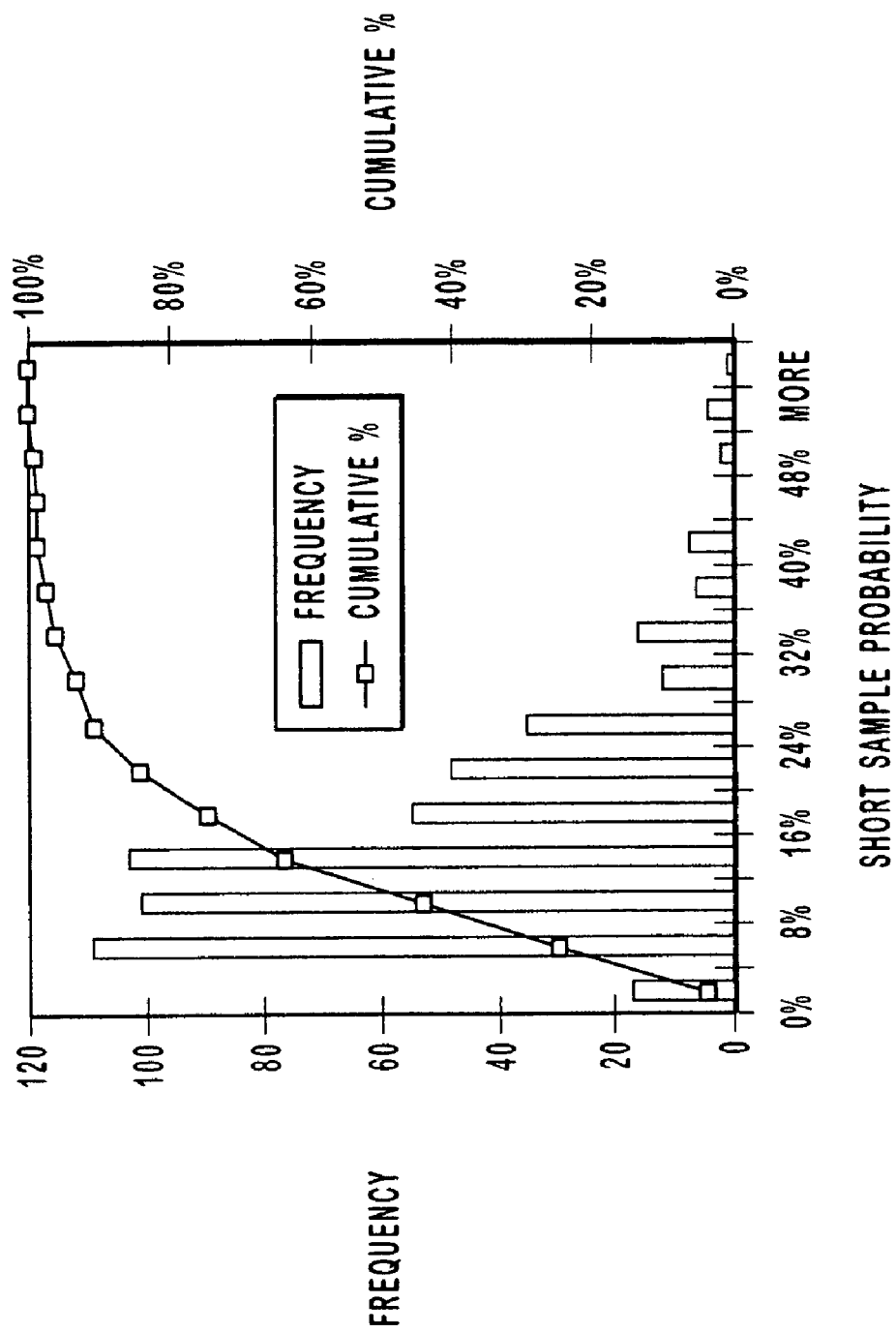
FIG. 12 is a graph depicting the frequency and cumulative frequency of short sample probability for a plurality of samples.

FIG. 12 (Example 54) illustrates how a short sample high probability threshold can be calculated. A statistically significant number of actual samples were analyzed for the basic metabolic panel collection of analytes and fluid data and the probability of short sample was calculated for each. The frequency for each probability is plotted in FIG. 12, along with the cumulative distribution of the population of short sample probability values. A threshold value can then be selected from this graph to use as a warning flag for high risk of short sample. For example, it may be decided that samples in the highest 5% for cumulative distribution are highly likely to be a short sample. Thus, because the cumulative distribution above 95% is approximately equal to a short sample probability of about 24%, any analytic test that yields a short sample probability of greater than 24% can be flagged as being a short sample.

Examples 55-56

Figure 13:
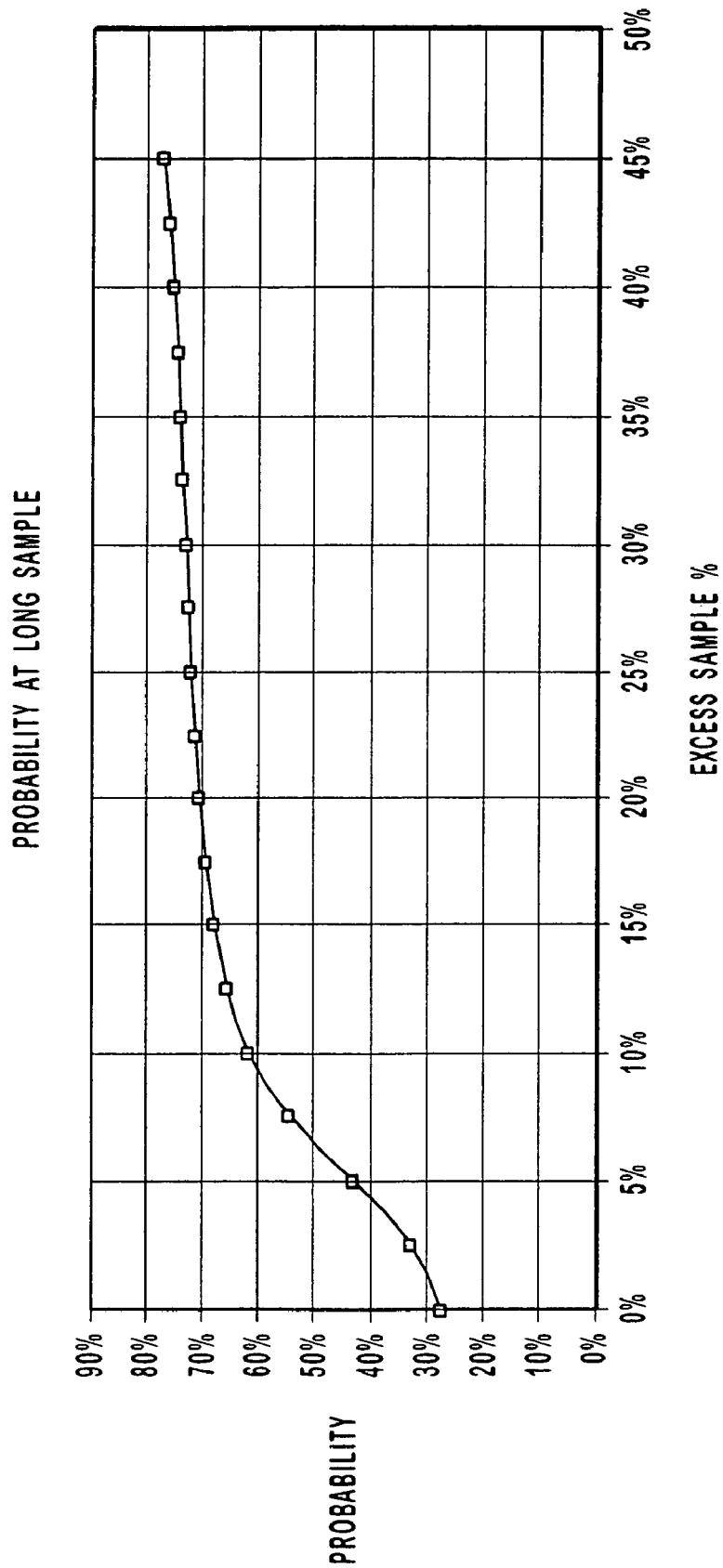
FIG. 13 is a graph depicting the probability of a long sample based on theoretically enlarged sample sizes.

The probability of a long sample can be determined for the basic metabolic panel combination of analytes and sample fluid datum: blood urea nitrogen, creatinine, glucose, creatine kinase, carbon dioxide, sodium, potassium, chlorine, osmolarity, and blood urea nitrogen/creatinine. A sample data set is obtained and then hypothetically multiplied times a sequentially increasing percent long sample amount, i.e. 102.5%, 105%, etc., to obtain higher values. This data is then plugged into equation 6 along with the values in Table 3 to determine long sample probabilities for each of the individual long sample datum. These long sample probabilities are then calculated according to equation 1 and the results are plotted as depicted in FIG. 13 (Example 55).

Figure 14:
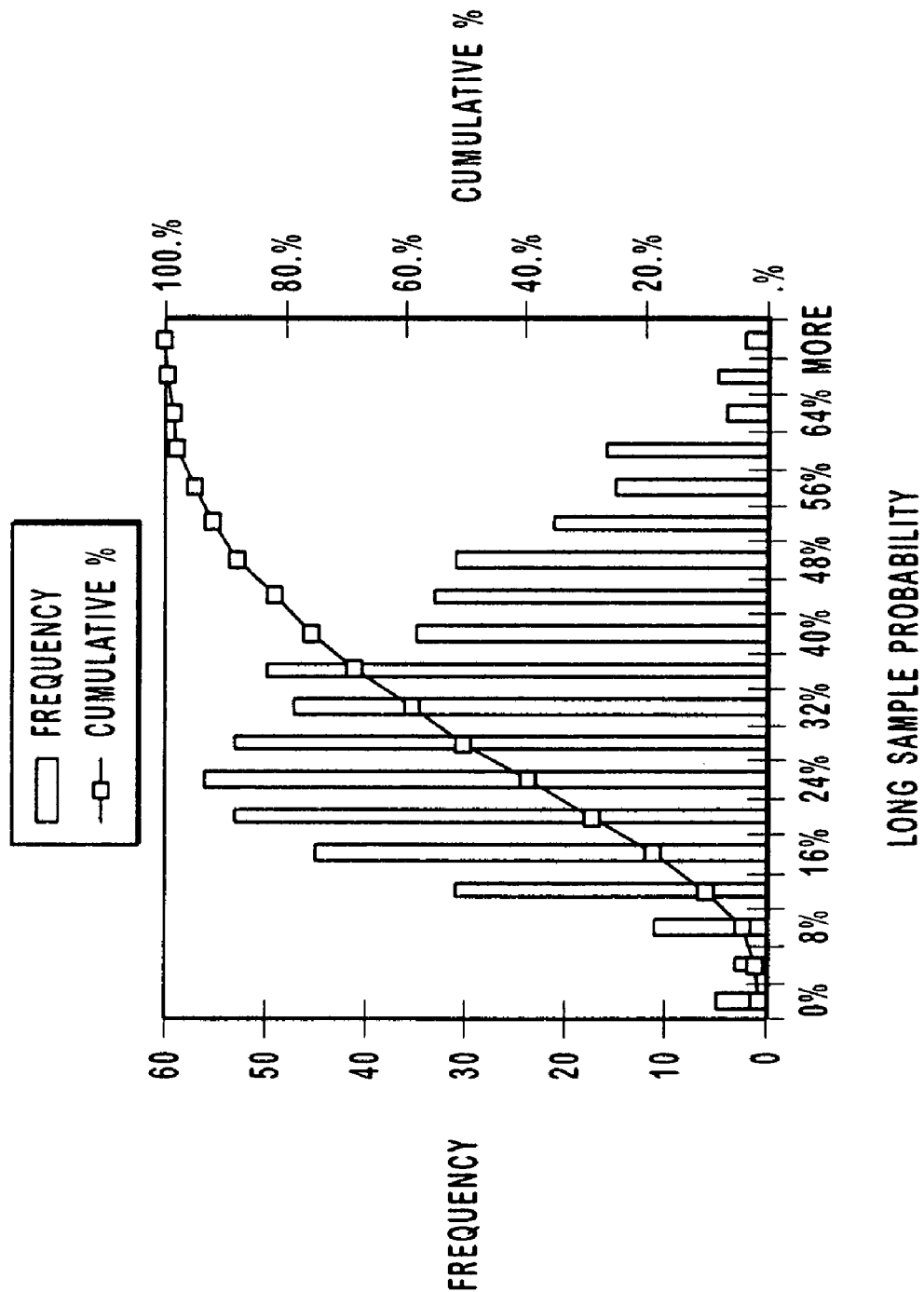
FIG. 14 is a graph depicting the frequency and cumulative frequency of long sample probability for a plurality of samples.

FIG. 14 (Example 56) illustrates how a long sample high probability threshold can be calculated. A statistically significant number of actual samples were analyzed for the basic metabolic panel collection of analytes and fluid data and the probability of long sample was calculated for each. The frequency for each probability is plotted in FIG. 14, along with the cumulative frequency. A threshold value can then be selected from this graph to use as a warning flag for high risk of long sample. For example, it may be decided that samples in the highest 5% for cumulative distribution are highly likely to be a long sample. Thus, because the cumulative distribution about 95% is approximately equal to a long sample probability of about 56%, any single analytic test that yields a long sample probability of greater than 56% can be flagged.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for analyzing a sample, the system comprising:
   an analyzer module configured to analyze a sample for at least one measurable characteristic to thereby generate sample data;
   a data module storing parameter data and relationship data, the parameter data comprising a distribution for the at least one measurable characteristic in a representative subject population, and the relationship data defining a relationship between the parameter data and the sample data; and
   an evaluation module in communication with the data module and the analyzer module, and programmed to use the parameter data, the relationship data, and the sample data to determine the probability that the sample is a short sample, a long sample, or an acceptable sample.

2. The system of claim 1, wherein the evaluation module further comprises:
   an identification module adapted to receive the sample data, the parameter data, and the relationship data; and
   a processing module for determining the probability that the sample is a short sample, a long sample, or an acceptable sample.

3. The system of claim 1, wherein the data module further comprises data representing one or more decision level parameters, wherein each decision level parameter defines a threshold probability level below which the sample is identified as either a short sample or a long sample.

4. The system of claim 3, further comprising an output module capable of notifying a user as to whether the sample is a short sample, a long sample, or an acceptable sample.

5. The system of claim 4, wherein the output module is a video display or LED.

6. The system of claim 1, wherein at least one measurable characteristic is the concentration of albumin, alkaline phosphatase, alanine aminotransferase, amylase, aspartate amino transferase, total bilirubin, blood urea nitrogen, calcium, cholesterol, creatinine, glucose, total protein, total protein/albumin, and blood urea nitrogen/creatinine, creatine kinase, carbon dioxide, sodium, potassium, or chlorine.

7. The system of claim 1, wherein the measurable characteristic(s) comprise one or more of osmolarity, alkalinity, and acidity.

8. The system of claim 1, wherein the measurable characteristic(s) comprise at least one contaminant found in water.

9. The system of claim 1, wherein at least one measurable characteristic is an antibody associated with a drug of abuse.

10. The system of claim 1, wherein the analyzer module comprises an optical analyzer.

11. The system of claim 1, wherein the analyzer module comprises an electrochemical analyzer.

12. The system of claim 1, wherein the analyzer is configured to analyze a sample for a plurality of measurable characteristics to thereby generate sample data, and the parameter data comprises a distribution for each of the measurable characteristics in a representative population.

13. The system of claim 12, wherein the plurality of measurable characteristics is a panel of electrolytes.

14. The system of claim 1, wherein the analyzer module comprises a centrifugal rotor.

15. The system of claim 1, wherein the analyzer module comprises a spectrophotometer.

16. The system of claim 1, wherein the analyzer module detects a color, fluorescence, and/or luminescence.

17. A system for analyzing a sample, the system comprising:
   an analyzer module configured to analyze a sample for at least one measurable characteristic to thereby generate sample data;
   a data module storing parameter data and relationship data, the parameter data comprising a distribution for the at least one measurable characteristic in a representative subject population, and the relationship data defining a relationship between the parameter data and the sample data; and
   an evaluation module in communication with the data module and the analyzer module, the evaluation module using the parameter data, the relationship data, and the sample data to determine the probability that the specimen is a short sample.

18. The system of claim 17, wherein the evaluation module further comprises:
   an identification module adapted to receive the sample data, the parameter data, and the relationship data; and
   a processing module for determining the probability that the sample is a short sample.

19. The system of claim 17, wherein the data module further comprises data representing decision level parameters, wherein the decision level parameters define a probability threshold level below which the sample is identified as a short sample.

20. The system of claim 19, further comprising an output module for notifying a user as to whether the sample is at least one of a short sample or an acceptable sample.

21. The system of claim 17, wherein the at least one measurable characteristic is the concentration of albumin, alkaline phosphatase, alanine aminotransferase, amylase, aspartate amino transferase, total bilirubin, blood urea nitrogen, calcium, cholesterol, creatinine, glucose, total protein, total protein/albumin, and blood urea nitrogen/creatinine, creatine kinase, carbon dioxide, sodium, potassium, or chlorine.

22. The system of claim 17, wherein the at least one measurable characteristic is a measurable characteristic of blood.

23. The system of claim 17, wherein the at least one measurable characteristic is a measurable characteristic of serum.

24. The system of claim 17, wherein the at least one measurable characteristic is a measurable characteristic of urine.

25. The system of claim 17, wherein the analyzer is configured to analyze a sample for a plurality of measurable characteristics to thereby generate sample data, and the parameter data comprises a distribution for each of the measurable characteristics in a representative population.

26. The system of claim 25, wherein the plurality of measurable characteristics is a panel of electrolytes.

27. The system of claim 17, wherein the analyzer module comprises a centrifugal rotor.

28. The system of claim 17, wherein the analyzer module comprises a spectrophotometer.

29. The system of claim 17, wherein the analyzer module detects a color, fluorescence, and/or luminescence.

30. The system of claim 17, wherein the output module is a video display or LED.

* * * * *